(12) United States Patent
Black

(10) Patent No.: US 9,440,066 B2
(45) Date of Patent: Sep. 13, 2016

(54) SYSTEMS AND METHODS FOR MAKING AND USING CONNECTOR ASSEMBLIES FOR IMPLANTABLE MEDICAL DEVICE SYSTEMS

(71) Applicant: BOSTON SCIENTIFIC NEUROMODULATION CORPORATION, Valencia, CA (US)

(72) Inventor: James Robert Black, Malibu, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 47 days.

(21) Appl. No.: 14/604,299

(22) Filed: Jan. 23, 2015

(65) Prior Publication Data

US 2015/0209575 A1 Jul. 30, 2015

Related U.S. Application Data

(60) Provisional application No. 61/932,074, filed on Jan. 27, 2014.

(51) Int. Cl.
*A61N 1/375* (2006.01)
*A61N 1/05* (2006.01)
*H01R 13/52* (2006.01)
*H01R 24/58* (2011.01)

(52) U.S. Cl.
CPC ........... *A61N 1/0551* (2013.01); *A61N 1/3752* (2013.01); *H01R 13/5224* (2013.01); *A61N 1/0558* (2013.01); *A61N 2001/0582* (2013.01); *H01R 24/58* (2013.01); *H01R 2201/12* (2013.01)

(58) Field of Classification Search
CPC .... A61N 1/0558; A61N 1/3752; A61N 1/05; A61N 2001/0582; H01R 2201/12
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,921,295 B2 * | 7/2005 | Sommer ............... A61N 1/056 439/668 |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |

(Continued)

*Primary Examiner* — George Evanisko
(74) *Attorney, Agent, or Firm* — Lowe Graham Jones PLLC; Bruce E. Black

(57) ABSTRACT

A lead extension for an electrical stimulation system includes a lead-extension body, terminals, and a connector. The connector includes a contact housing and a gasket housing. Multiple connector contacts are disposed in the contact housing and are coupled to the terminals. A retention member is disposed along one end of the contact housing and is receivable by a retention socket defined in the gasket housing. A deformable gasket is disposed in the retention socket. A lumen extends through the connector and is suitable for receiving an electrical stimulation lead. The received lead is retained in the lumen by using the retention member to compress the gasket along a longitudinal length of the connector. The longitudinal compression of the gasket causes a corresponding radial expansion of the gasket, which retains the electrical stimulation lead within the lumen.

16 Claims, 13 Drawing Sheets

(56) References Cited

U.S. PATENT DOCUMENTS

| | | |
|---|---|---|
| 8,364,278 B2 | 1/2013 | Pianca et al. |
| 2007/0150036 A1 | 6/2007 | Anderson |
| 2010/0268298 A1 | 10/2010 | Moffitt et al. |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |

\* cited by examiner

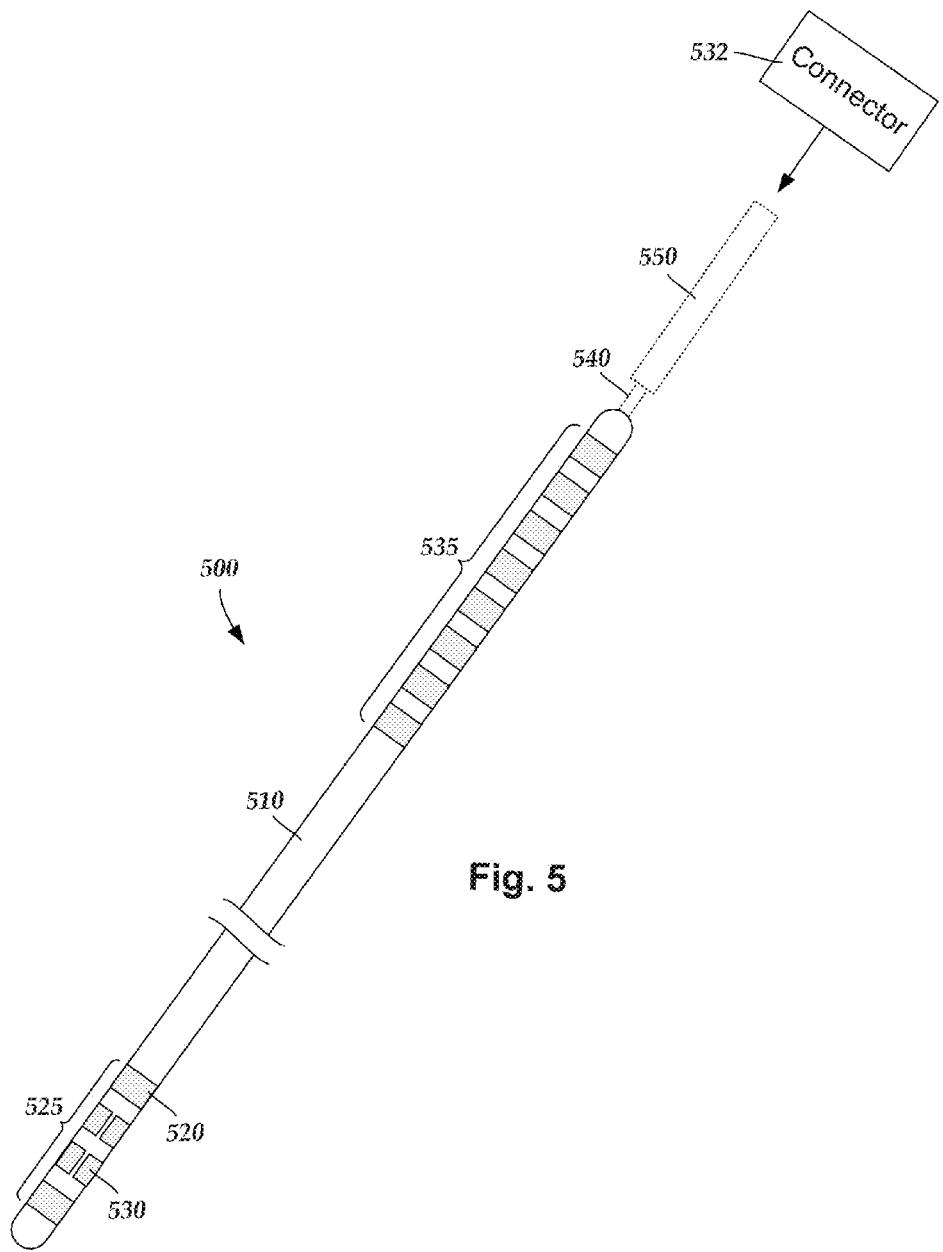

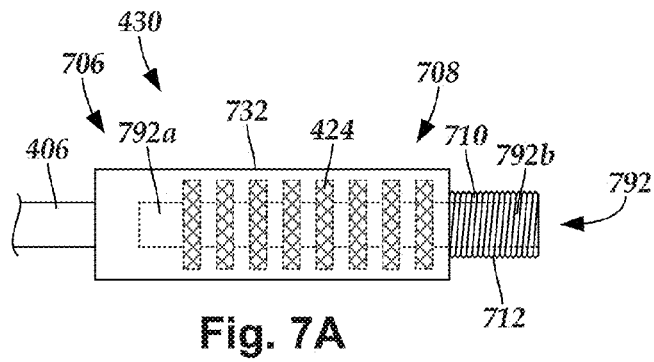
Fig. 7A
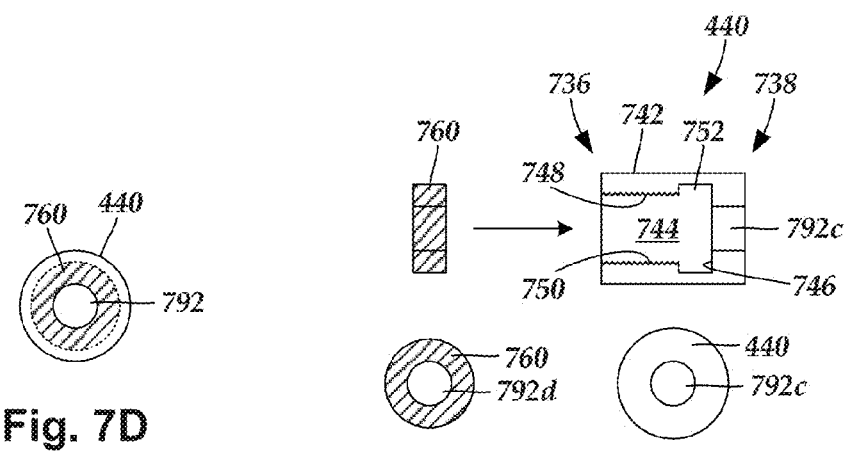
Fig. 7D
Fig. 7B
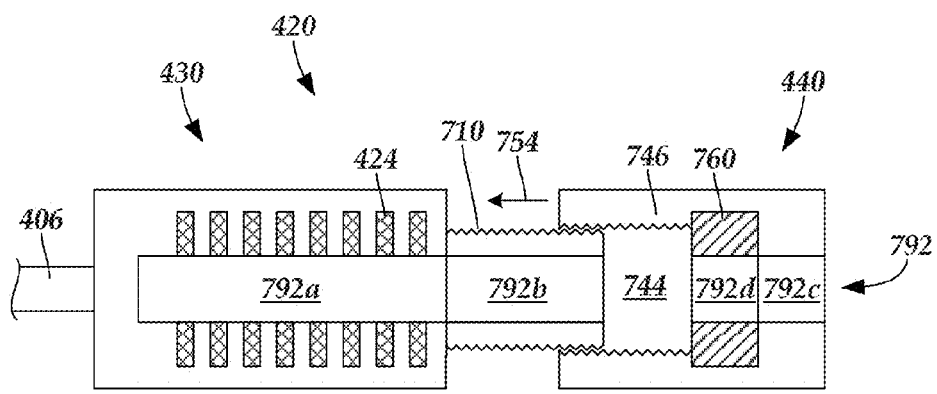
Fig. 7C

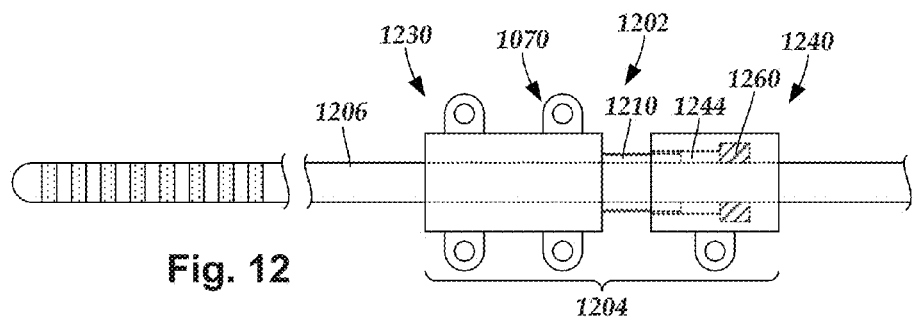
Fig. 12
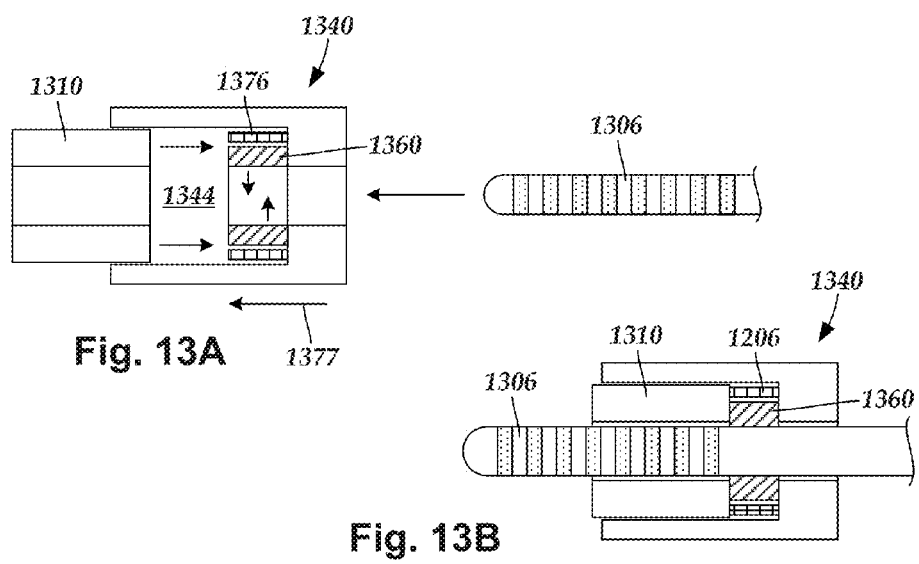
Fig. 13A
Fig. 13B
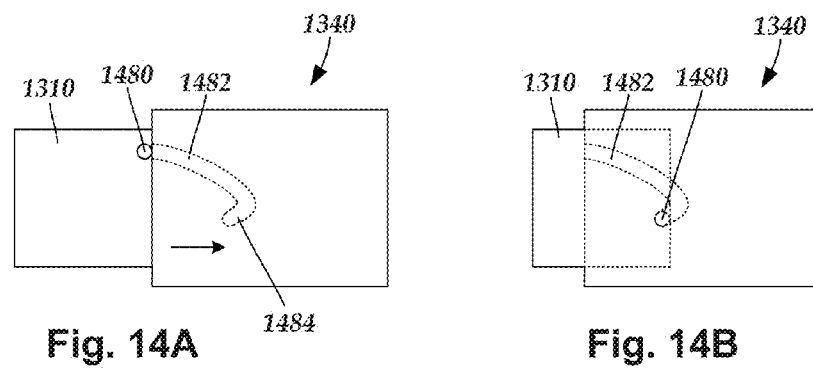
Fig. 14A
Fig. 14B

SYSTEMS AND METHODS FOR MAKING AND USING CONNECTOR ASSEMBLIES FOR IMPLANTABLE MEDICAL DEVICE SYSTEMS

CROSS-REFERENCE TO RELATED APPLICATIONS

This application claims the benefit under 35 U.S.C. §119 (e) of U.S. Provisional Patent Application Ser. No. 61/932,074, filed Jan. 27, 2014, which is incorporated herein by reference.

FIELD

The present invention is directed to the area of implantable medical device systems and methods of making and using the systems. The present invention is also directed to connector assemblies for devices of the systems, as well as methods of making and using the connector assemblies and implantable medical device systems.

BACKGROUND

Implantable medical device systems, such as electrical stimulation systems, have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Implantable electrical stimulation systems can also be used for providing other types of stimulation including, for example, deep brain stimulation. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

In one embodiment, a lead extension for an electrical stimulation system includes a lead extension body having a distal end portion and a proximal end portion, and a plurality of terminals disposed along the proximal end portion of the lead extension body. In addition, the electrical stimulation system includes a connector disposed along the distal end portion of the lead extension body. The connector has an exterior surface and a longitudinal length. The connector includes a contact housing having a first end portion, an opposing second end portion, and an exterior surface. The contact housing defines a contact-housing lumen and includes a plurality of connector contacts disposed in the contact housing and exposed to the contact-housing lumen. In addition, the connector includes a retention member disposed along the second end portion of the contact housing. The retention member defines a retention-member lumen extending along an entire length of the retention member. Further, the connector includes a gasket housing coupled to the second end portion of the contact housing. The gasket housing has a first end, an opposing second end, and an exterior surface. Furthermore, the connector includes a retention socket defined along the first end of the gasket housing. The retention socket includes a rear wall and a side wall. The retention socket is configured and arranged for receiving the retention member. A gasket-housing lumen extends between the exterior surface of the gasket housing and the rear wall of the retention socket. In addition, a deformable gasket is disposed in the retention socket and defines a gasket lumen. The retention-member lumen, the contact-housing lumen, the gasket-housing lumen, and the gasket lumen are longitudinally-aligned with one another along the longitudinal length of the connector and collectively form a lead lumen configured and arranged for receiving a portion of an electrical stimulation lead. The gasket housing is configured and arranged to tighten toward the contact housing by advancing the retention member into the retention socket and compressing the deformable gasket along the longitudinal length of the connector. The longitudinal compression of the gasket causes a corresponding radial expansion of the gasket into the lead lumen. The radial expansion of the gasket retains a portion of an electrical stimulation lead within the lead lumen when the electrical stimulation lead is received by the lead lumen. Further, a plurality of conductors electrically couples the plurality of terminals to the plurality of connector contacts.

In another embodiment, a control module for an electrical stimulation system includes an electronics housing, an electronic subassembly disposed in the electronics housing, and a connector coupled to the electronics housing. The connector is configured and arranged for receiving an electrical stimulation lead. The connector includes a contact housing having a first end portion, an opposing second end portion, and an exterior surface. The contact housing defines a contact-housing lumen and includes a plurality of connector contacts disposed in the contact housing and exposed to the contact-housing lumen. The plurality of connector contacts are electrically coupled to the electronic subassembly. The contact housing also includes a retention member disposed along the second end portion of the contact housing. The retention member defines a retention-member lumen extending along an entire length of the retention member. The contact housing further includes a gasket housing coupled to the second end portion of the contact housing. The gasket housing has a first end, an opposing second end, and an exterior surface. Furthermore, the contact housing includes a retention socket defined along the first end of the gasket housing. The retention socket includes a rear wall and a side wall. The retention socket is configured and arranged for receiving the retention member. The contact housing also includes a gasket-housing lumen extending between the exterior surface of the gasket housing and the rear wall of the retention socket, and a deformable gasket disposed in the retention socket and defining a gasket lumen. The retention-member lumen, the contact-housing lumen, the gasket-housing lumen, and the gasket lumen are longitudinally-aligned with one another along the longitudinal length of the connector and collectively form a lead lumen configured and arranged for receiving a portion of an electrical stimulation lead. The gasket housing is configured and arranged to tighten toward the contact housing by advancing the retention member into the retention socket and compressing the deformable gasket along the longitudinal length of the connector. The longitudinal compression of the gasket causes a corresponding radial expansion of the gasket into the lead lumen. The radial expansion of the gasket retains a portion of an electrical stimulation lead within the lead lumen when the electrical stimulation lead is received by the lead lumen.

In yet another embodiment, a lead anchor for an implantable electrical stimulation system includes an anchor body having a longitudinal length and an exterior surface. The anchor body includes a retention-member housing and a gasket housing. The retention-member housing has a first end portion, an opposing second end portion, and an exterior surface. The retention-member housing defines a retention-member-housing lumen. The gasket housing is coupled to the second end portion of the retention-member housing. The gasket housing includes a first end, an opposing second end, and an exterior surface. At least one anchoring unit is disposed along the exterior surface of the anchor body. A retention member is disposed along the second end portion of the retention-member housing. The retention member defines a retention-member lumen extending along an entire length of the retention member. A retention socket is defined along the first end of the gasket housing. The retention socket is configured and arranged for receiving the retention member. The gasket housing includes a rear wall and a side wall. A gasket-housing lumen extends between the exterior surface of the gasket housing and the rear wall of the retention socket. Additionally, a deformable gasket is disposed in the gasket housing and defines a gasket lumen. The retention-member-housing lumen, the retention-member lumen, the gasket-housing lumen, and the gasket lumen are longitudinally-aligned with one another along the longitudinal length of the anchor body and collectively form a lead lumen configured and arranged for receiving a portion of an electrical stimulation lead. The gasket housing is configured and arranged to tighten toward the retention-member housing by advancing the retention member into the retention socket and compressing the deformable gasket along the longitudinal length of the anchor body. The longitudinal compression of the gasket causes a corresponding radial expansion of the gasket into the lead lumen. The radial expansion of the gasket retains a portion of an electrical stimulation lead within the lead lumen when the electrical stimulation lead is received by the lead lumen.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5 is a schematic side view of one embodiment of a device for brain stimulation, according to the invention;

FIG. 7A is a schematic side view of one embodiment of the contact housing of the connector of FIG. 4, the contact housing including a retention member and a lead lumen extending through the retention member and into the contact housing, according to the invention;

FIG. 7B includes a schematic longitudinal cross-sectional view of one embodiment of the gasket housing of the connector of FIG. 4 and a gasket suitable for insertion into the gasket housing, as well as schematic end views of the gasket housing and the gasket, the gasket and gasket housing both defining lead lumens extending therethrough, according to the invention;

FIG. 7C is a schematic longitudinal cross-sectional view of one embodiment of the contact housing of FIG. 7A partially coupled to the gasket housing of FIG. 7B via the retention member of the contact housing and the retention socket of the gasket housing to form the connector of FIG. 4, the contact housing and the gasket housing collectively forming a lead lumen extending through the gasket housing, the retention member, and at least a portion of the contact housing, according to the invention;

FIG. 7D is a schematic end view of one embodiment of the connector of FIG. 7C, according to the invention;

FIG. 12 is a schematic side view of one embodiment of a lead body inserted into a lead anchor, the lead anchor including a retention member that is disposed along a retention-member housing and that couples with a gasket disposed in a retention socket of a gasket housing, according to the invention;

FIG. 13A is a schematic longitudinal cross-sectional view of another embodiment of a retention member suitable for inserting into a retention socket of a gasket housing, the gasket housing including a gasket and a biasing member disposed in the retention socket, according to the invention;

FIG. 13B is a schematic longitudinal cross-sectional view of one embodiment of the lead body of FIG. 13A inserted into retention member and gasket housing of FIG. 13A with the gasket of the gasket housing tightened around a portion of the lead body to retain the lead body within a lead lumen extending through the retention member and gasket housing, according to the invention;

FIG. 14A is a schematic side view of one embodiment of the retention member and the gasket housing of FIG. 13A, the gasket housing defining a passageway along a side wall of the retention socket of the gasket housing, the passageway suitable for receiving a protrusion disposed along the retention member, according to the invention;

FIG. 14B is a schematic side view of one embodiment of the retention member and the gasket housing of FIG. 14A, with the protrusion of the retention member received by the passageway of the gasket housing, according to the invention.

DETAILED DESCRIPTION

The present invention is directed to the area of implantable medical device systems and methods of making and using the systems. The present invention is also directed to connector assemblies for devices of the systems, as well as methods of making and using the connector assemblies and implantable medical device systems.

Suitable implantable electrical stimulation systems include, but are not limited to, a lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
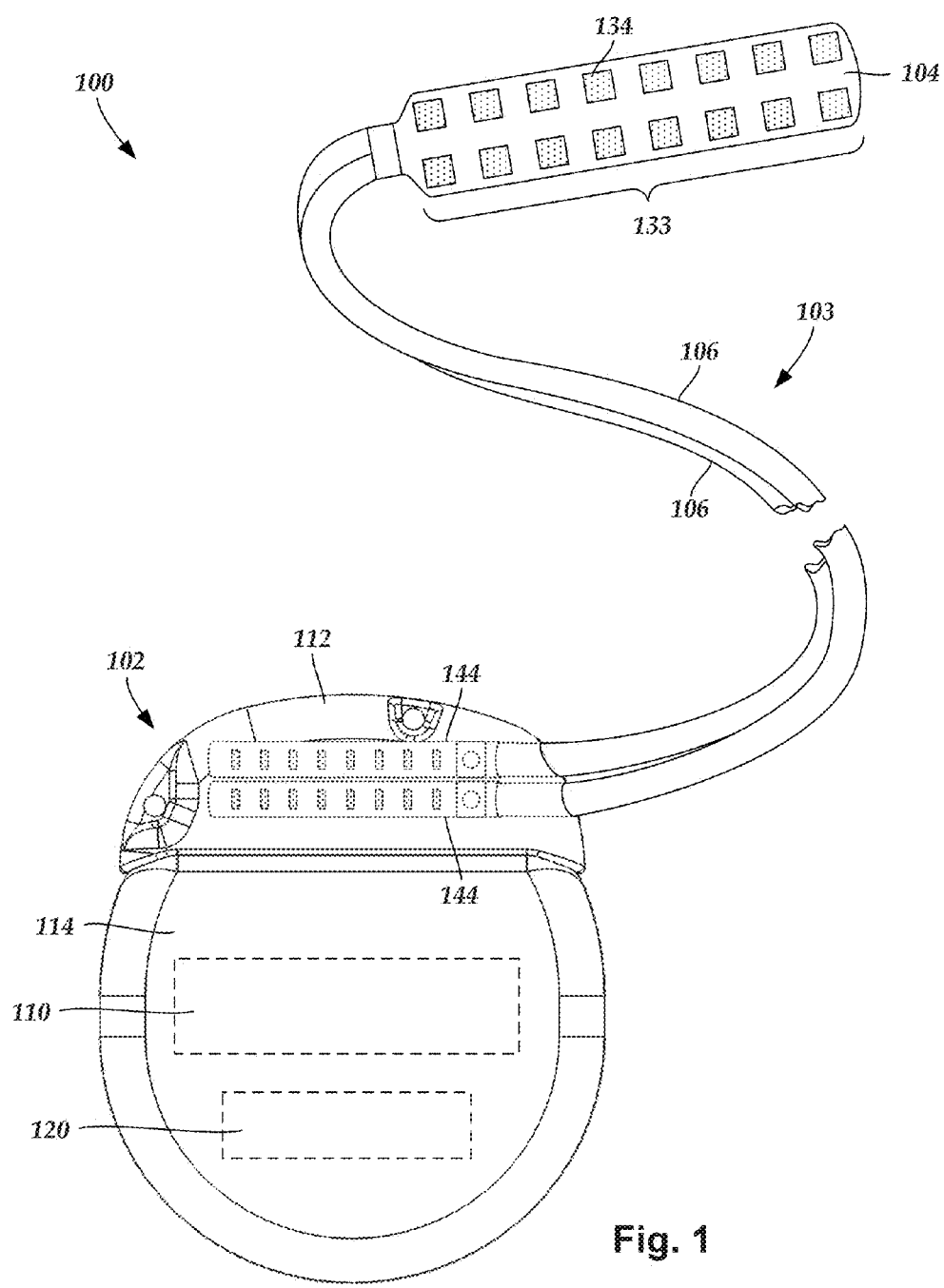
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight, or more lead bodies 106. An array 133 of electrodes, such as electrode 134, is disposed on the paddle body 104, and an array of terminals (e.g., 310 in FIG. 3) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
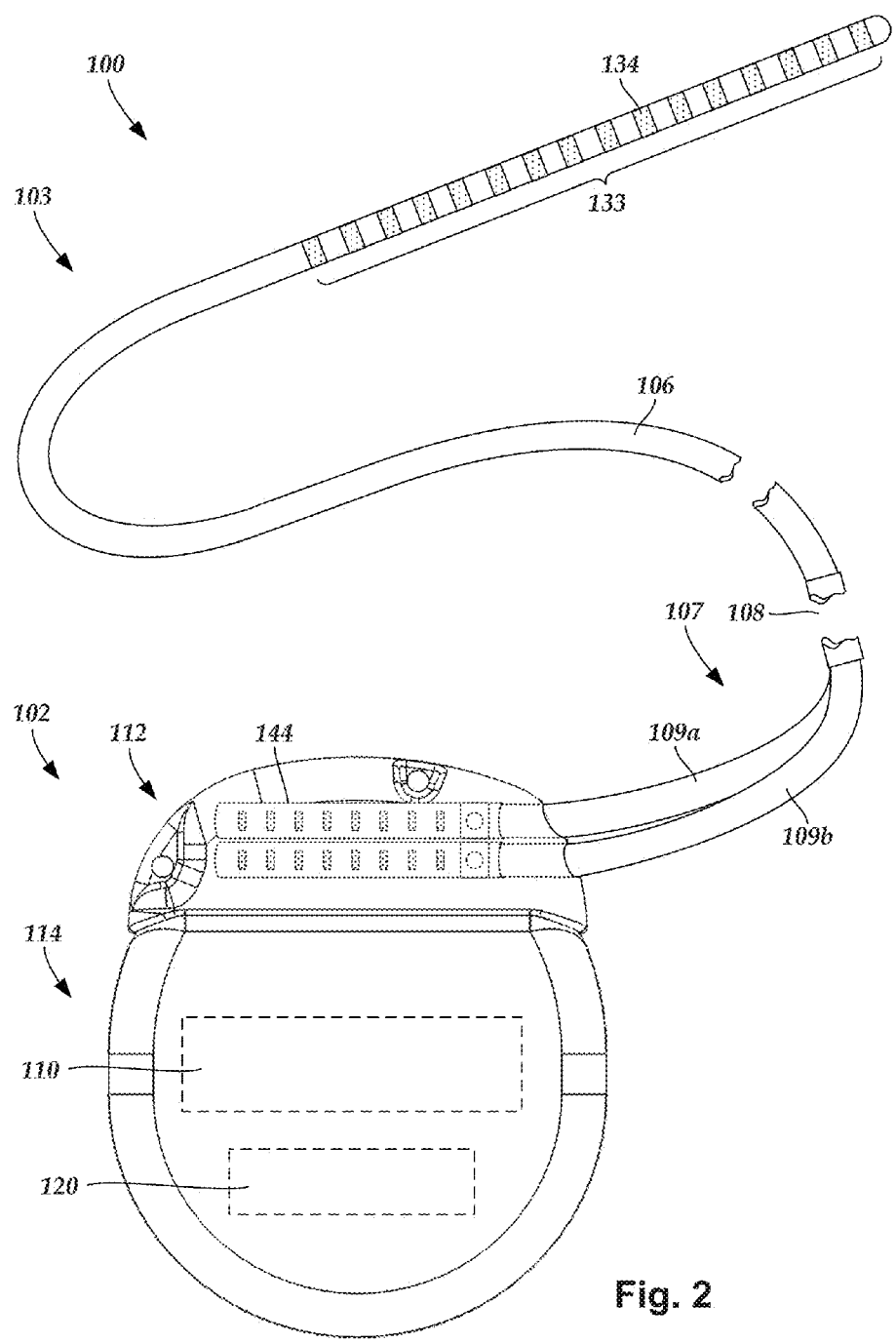
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices. For example, in at least some embodiments one or more lead extensions (402 in FIG. 4 and in other figures) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 suitable for facilitating coupling of the lead 103 to the control module 102. The splitter 107 includes a splitter connector 108 for coupling to a proximal end of the lead 103, and one or more splitter tails 109*a* and 109*b* for coupling to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently, or detachably, coupled together.

Figure 3:
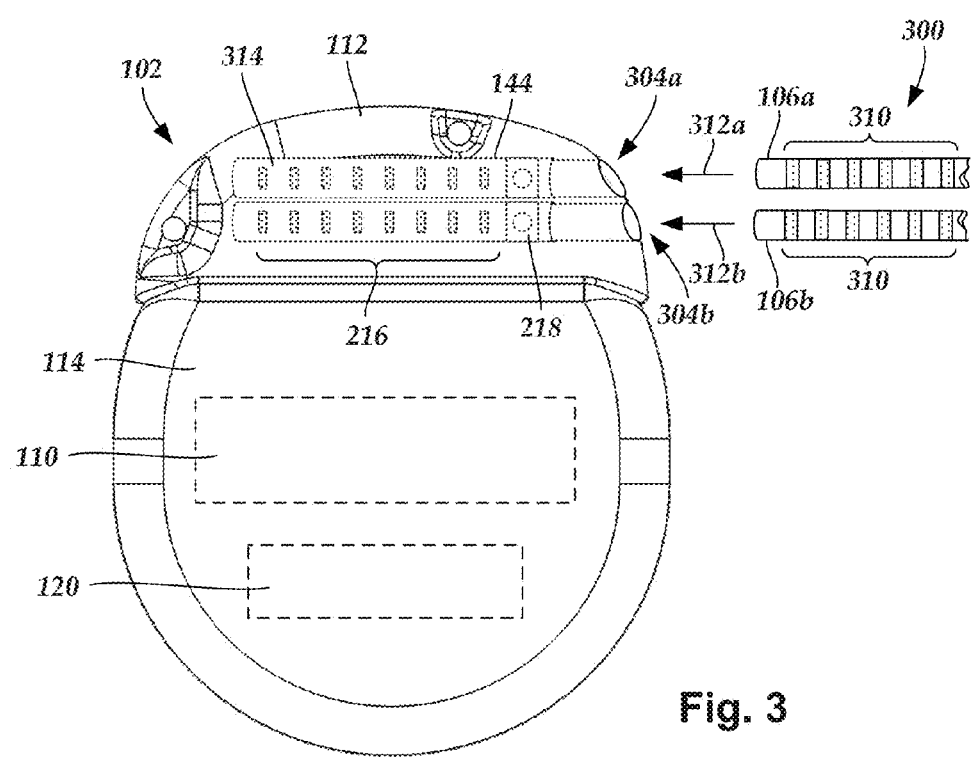
FIG. 3 is a schematic view of one embodiment of the control module of FIG. 1 configured and arranged to electrically couple to an elongated device, according to the invention.

Terminals (e.g., 310 in FIG. 3) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3). The connector contacts are disposed in connectors (e.g., 144 in FIGS. 1-4; 420 in FIGS. 4, 7D-8D, and 9; 1020 in FIG. 10; and 1120 in FIG. 11) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3 illustrates one embodiment of a proximal end of one or more elongated devices 300 configured and arranged for coupling to one embodiment of the control module connector 144. The one or more elongated devices may include, for example, one or more of the lead bodies (106 in FIG. 1), one or more intermediate devices (e.g., a splitter, the lead extension (402 in FIG. 4), an adaptor, or the like or combinations thereof), or a combination thereof.

The control module connector 144 defines at least one port into which a proximal end of the elongated device 300 can be inserted, as shown by directional arrows 312*a* and 312*b*. In FIG. 3 (and in other figures), the connector housing 112 is shown having two ports 304*a* and 304*b*. The connector housing 112 can define any suitable number of ports including, for example, one, two, three, four, five, six, seven, eight, or more ports.

The control module connector 144 also includes a plurality of connector contacts, such as connector contact 314, disposed within each port 304*a* and 304*b*. When the elongated device 300 is inserted into the ports 304*a* and 304*b*, the connector contacts 314 can be aligned with a plurality of terminals 310 disposed along the proximal end(s) of the elongated device(s) 300 to electrically couple the control module 102 to the electrodes (134 in FIG. 1) disposed on the paddle body 104 of the lead 103. Examples of connectors in control modules are found in, for example, U.S. Pat. Nos. 7,244,150 and 8,224,450, which are incorporated by reference.

Figure 4:
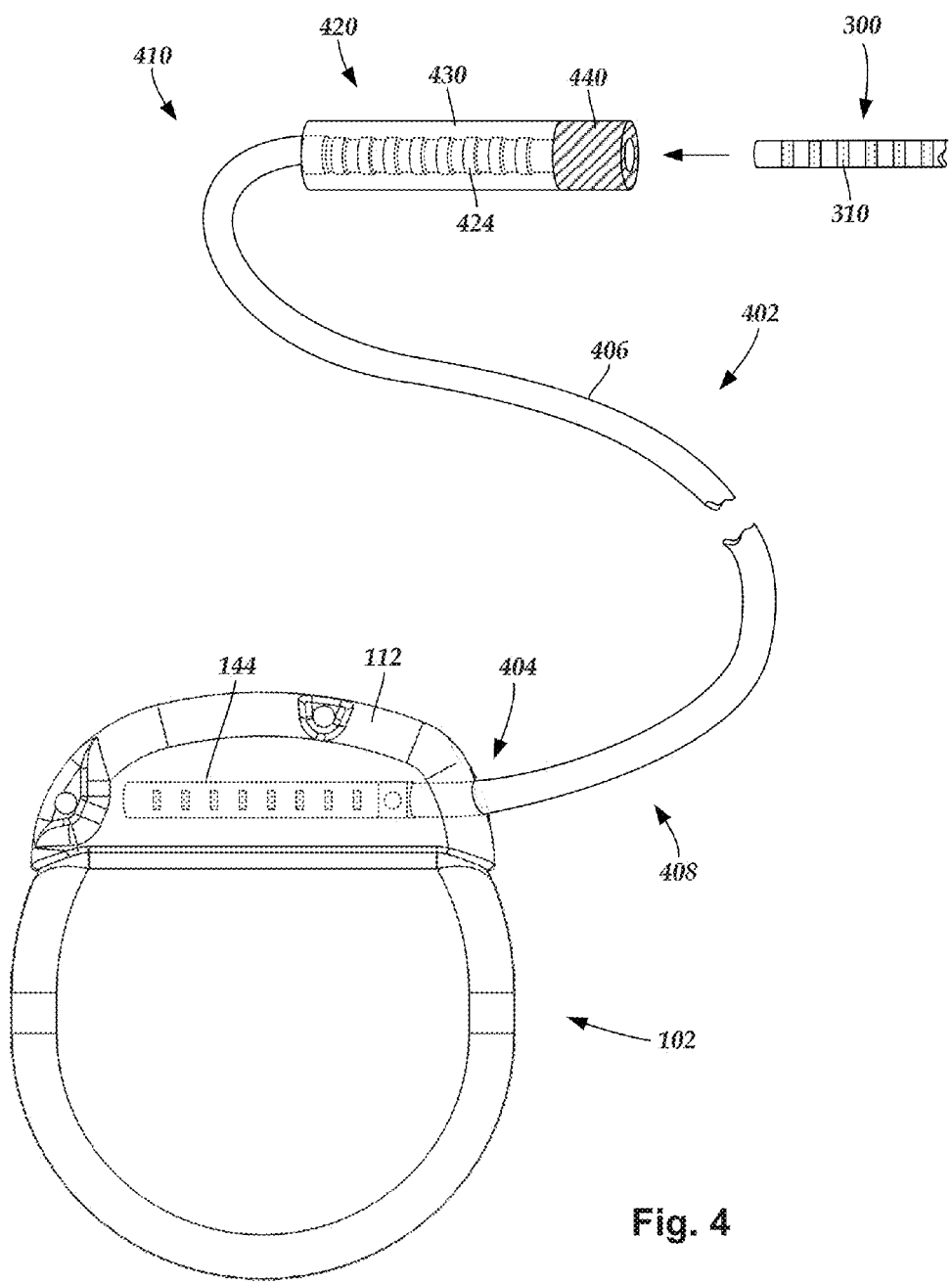
FIG. 4 is a schematic view of one embodiment of a lead extension configured and arranged to electrically couple the elongated device of FIG. 2 to the control module of FIG. 1 via a connector that includes a gasket housing coupled to a contact housing, according to the invention.

In at least some embodiments, the elongated device 300 (e.g., one of the lead bodies 106 of FIGS. 1 and 2, the splitter 207, an adaptor, another lead extension, or the like or combinations thereof) is coupled to the control module 102 via a lead extension. FIG. 4 illustrates one embodiment of a lead extension 402 coupled to the control module 102 via a port 404 defined in the control module connector 144. The lead extension 402 is suitable for receiving one or more elongated devices 300. In FIG. 4, the lead extension 402 is shown being suitable for receiving a single elongated device 300.

The lead extension 402 has a body 406 with a proximal end portion 408 and a distal end portion 410. As will be discussed in more detail below (see e.g., FIGS. 7A-14B), a connector 420 is disposed along the distal end portion 410 of the lead extension 402. The connector 420 includes a contact housing 430 coupleable to a gasket housing 440. A plurality of connector contacts, such as connector contact 424, is disposed in the contact housing 430. The connector contacts 424 are suitable for coupling with terminals, such as terminal 310, of the elongated device 300 when the proximal end portion of the elongated device 300 is inserted into the connector 420. The gasket housing 440 facilitates retention of the elongated device 300 when the elongated device 300 is received by the connector 420.

In at least some embodiments, the proximal end portion 408 of the lead extension 402 is similarly configured and arranged as a proximal end portion of the lead 103 (or other elongated device 300). The lead extension 402 may include a plurality of electrically conductive wires (not shown) that electrically couple the connector contacts 424 to the proximal end portion 408 of the lead extension 402.

In at least some embodiments, the conductive wires disposed in the lead extension 402 can be electrically coupled to a plurality of terminals (not shown) disposed along the proximal end portion 408 of the lead extension 402. In at least some embodiments, the proximal end portion 408 of the lead extension 402 is configured and arranged for insertion into a connector disposed in another lead extension (or another intermediate device). In other embodiments (and as shown in FIG. 4), the proximal end portion 408 of the lead extension 402 is configured and arranged for insertion into the control module connector 144.

Figure 6A:
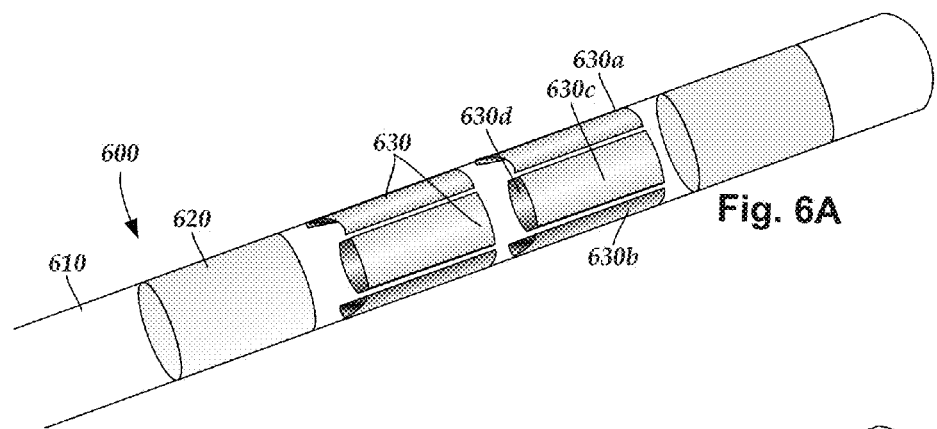
FIG. 6A is a perspective view of an embodiment of a portion of a lead having a plurality of segmented electrodes, according to the invention.
Figure 6B:
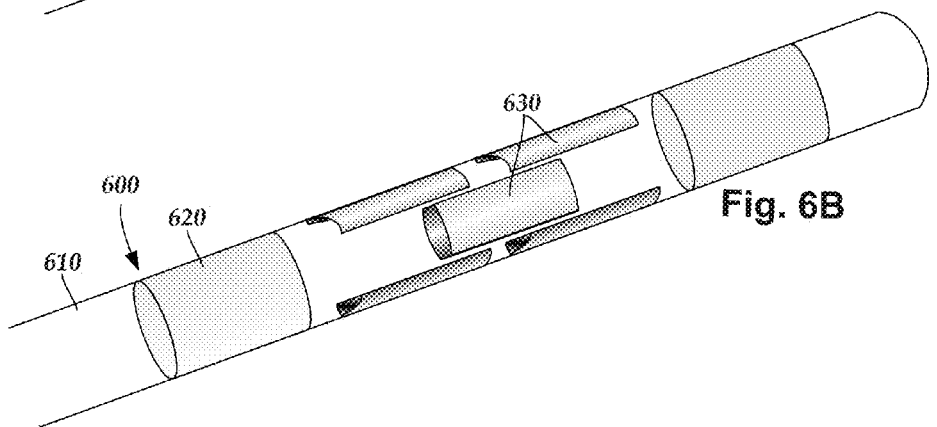
FIG. 6B is a perspective view of a second embodiment of a portion of a lead having a plurality of segmented electrodes, according to the invention.
Figure 6C:
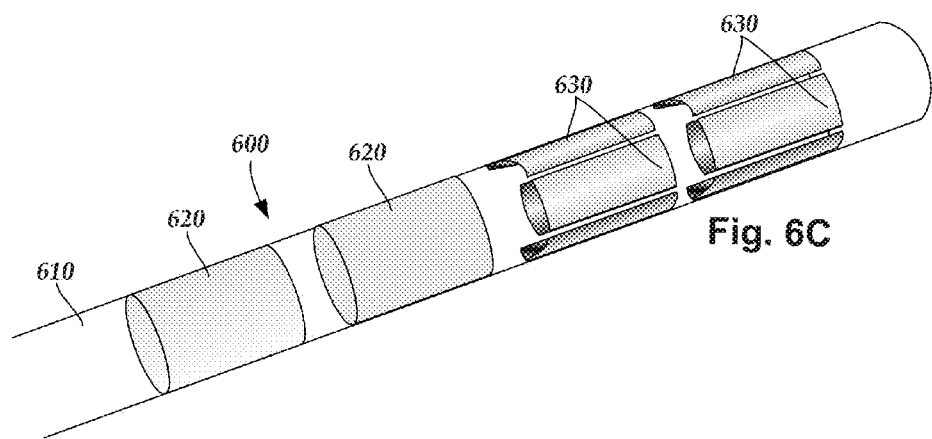
FIG. 6C is a perspective view of a third embodiment of a portion of a lead having a plurality of segmented electrodes, according to the invention.
Figure 6D:
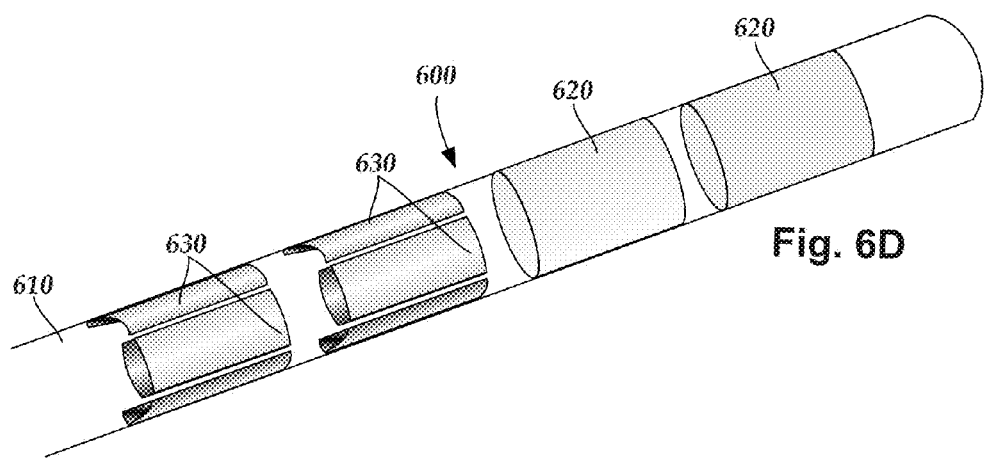
FIG. 6D is a perspective view of a fourth embodiment of a portion of a lead having a plurality of segmented electrodes, according to the invention.
Figure 6E:
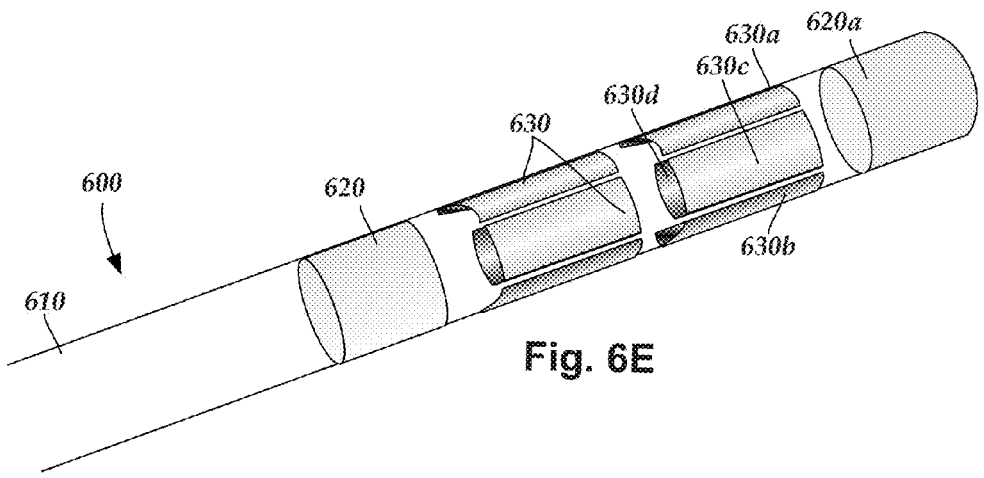
FIG. 6E is a perspective view of a fifth embodiment of a portion of a lead having a plurality of segmented electrodes, according to the invention.

Turning to FIGS. 5-6E, in some embodiments leads (e.g., percutaneous leads) are used in electrical stimulation systems designed for brain stimulation. FIG. 5 illustrates one embodiment of a device 500 for brain stimulation. The device includes a lead 510, a plurality of electrodes 525 disposed at least partially about a circumference of the lead 510, a plurality of terminals 535, a connector 532 for connection of the electrodes to a control unit, and a stylet 540 for assisting in insertion and positioning of the lead in the patient's brain. The stylet 540 can be made of a rigid material. Examples of suitable materials for the stylet include, but are not limited to, tungsten, stainless steel, and plastic. The stylet 540 may have a handle 550 to assist insertion into the lead 510, as well as rotation of the stylet 540 and lead 510. The connector 532 fits over a proximal end of the lead 510, preferably after removal of the stylet 540.

The control unit (not shown) is typically an implantable pulse generator that can be implanted into a patient's body, for example, below the patient's clavicle area. The pulse generator can have, for example, eight stimulation channels that may be independently programmable to control the magnitude of the current stimulus from each channel. In some cases, the pulse generator can have more or fewer than eight stimulation channels (e.g., 4-, 6-, 16-, 32-, or more stimulation channels). The control unit can have one, two, three, four, or more connector ports, for receiving the plurality of terminals 535 at the proximal end of the lead 510.

In one example of operation, access to the desired position in the brain can be accomplished by drilling a hole in the patient's skull or cranium with a cranial drill (commonly referred to as a burr), and coagulating and incising the dura mater, or brain covering. The lead 510 can be inserted into the cranium and brain tissue with the assistance of the stylet 540. The lead 510 can be guided to the target location within the brain using, for example, a stereotactic frame and a microdrive motor system. In some embodiments, the microdrive motor system is fully or partially automatic. The microdrive motor system may be configured to perform one or more the following actions (alone or in combination): insert the lead 510, retract the lead 510, or rotate the lead 510.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 510 for deep brain stimulation can include stimulation electrodes, recording electrodes, or both. In at least some embodiments, the lead 510 is rotatable so that the stimulation electrodes can be aligned with the target neurons after the neurons have been located using the recording electrodes.

Stimulation electrodes may be disposed on the circumference of the lead 510 to stimulate the target neurons. Stimulation electrodes may be ring-shaped so that current projects from each electrode equally in every direction from the position of the electrode along a length of the lead 510. Ring electrodes typically do not enable stimulus current to be directed from only a limited angular range around of the lead. Segmented electrodes, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 500 includes a lead body 510, one or more optional ring electrodes 520, and a plurality of sets of segmented electrodes 530. The lead body 510 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 500 may be in contact with body tissue for extended periods of time. In at least some embodiments, the lead 500 has a cross-sectional diameter of no more than 1.5 mm and may be in the range of 0.5 to 1.5 mm. In at least some embodiments, the lead 500 has a length of at least 10 cm and the length of the lead 500 may be in the range of 10 to 70 cm.

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 520 can be disposed on any part of the lead body 510, usually along a distal end portion of the lead 500. In FIG. 5, the lead 500 includes two ring electrodes 520. Any number of ring electrodes 520 can be disposed along the length of the lead body 510 including, for example, one, two three, four, five, six, seven, eight, nine, ten, eleven, twelve, thirteen, fourteen, fifteen, sixteen, or more ring electrodes 520. It will be understood that any number of ring electrodes can be disposed along the length of the lead body 510. In some embodiments, the ring electrodes 520 are substantially cylindrical and wrap around the entire circumference of the lead body 510. In some embodiments, the outer diameters of the ring electrodes 520 are substantially equal to the outer diameter of the lead body 510. The length of the ring electrodes 520 may vary according to the desired treatment and the location of the target neurons. In some embodiments the length of the ring electrodes 520 are less than or equal to the diameters of the ring electrodes 520. In other embodiments, the lengths of the ring electrodes 520 are greater than the diameters of the ring electrodes 520. As discussed in more detail below, the distal-most ring electrode 520 may be a tip electrode (see e.g., tip electrode 620a of FIG. 6E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Application Publication Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference.

The lead 500 is shown having a plurality of segmented electrodes 530. Any number of segmented electrodes 530 may be disposed on the lead body 510 including, for example, one, two three, four, five, six, seven, eight, nine, ten, eleven, twelve, thirteen, fourteen, fifteen, sixteen, or more segmented electrodes 530. It will be understood that any number of segmented electrodes 530 may be disposed along the length of the lead body 510. A segmented electrode 530 typically extends only 75%, 67%, 60%, 50%, 40%, 33%, 25%, 20%, 17%, 15%, or less around the circumference of the lead.

The segmented electrodes 530 may be grouped into sets of segmented electrodes, where each set is disposed around a circumference of the lead 500 at a particular longitudinal portion of the lead 500. The lead 500 may have any number segmented electrodes 530 in a given set of segmented electrodes. The lead 500 may have one, two, three, four, five, six, seven, eight, or more segmented electrodes 530 in a given set. In at least some embodiments, each set of segmented electrodes 530 of the lead 500 contains the same number of segmented electrodes 530. The segmented electrodes 530 disposed on the lead 500 may include a different number of electrodes than at least one other set of segmented electrodes 530 disposed on the lead 500.

The segmented electrodes 530 may vary in size and shape. In some embodiments, the segmented electrodes 530 are all of the same size, shape, diameter, width, or area or any combination thereof. In some embodiments, the segmented electrodes 530 of each circumferential set (or even all segmented electrodes disposed on the lead 500) may be identical in size and shape.

Each set of segmented electrodes 530 may be disposed around the circumference of the lead body 510 to form a substantially cylindrical shape around the lead body 510. The spacing between individual electrodes of a given set of the segmented electrodes may be the same, or different from, the spacing between individual electrodes of another set of segmented electrodes on the lead 500. In at least some embodiments, equal spaces, gaps, or cutouts are disposed between each segmented electrode 530 around the circumference of the lead body 510. In other embodiments, the spaces, gaps, or cutouts between the segmented electrodes 530 may differ in size or shape. In other embodiments, the spaces, gaps, or cutouts between segmented electrodes 530 may be uniform for a particular set of the segmented electrodes 530, or for all sets of the segmented electrodes 530. The sets of segmented electrodes 530 may be positioned in irregular or regular intervals along a length the lead body 510.

Conductor wires that attach to the ring electrodes 520 or segmented electrodes 530 extend along the lead body 510. These conductor wires may extend through the material of the lead 500 or along one or more lumens defined by the lead 500, or both. The conductor wires are presented at a connector (via terminals) for coupling of the electrodes 520, 530 to a control unit (not shown).

When the lead 500 includes both ring electrodes 520 and segmented electrodes 530, the ring electrodes 520 and the segmented electrodes 530 may be arranged in any suitable configuration. For example, when the lead 500 includes two sets of ring electrodes 520 and two sets of segmented electrodes 530, the ring electrodes 520 can flank the two sets of segmented electrodes 530 (see e.g., FIG. 5). Alternately, the two sets of ring electrodes 520 can be disposed proximal to the two sets of segmented electrodes 530 (see e.g., FIG. 6C), or the two sets of ring electrodes 520 can be disposed distal to the two sets of segmented electrodes 530 (see e.g., FIG. 6D). One of the ring electrodes can be a tip electrode (see, tip electrode 620a of FIG. 6E). It will be understood that other configurations are possible as well (e.g., alternating ring and segmented electrodes, or the like).

By varying the location of the segmented electrodes 530, different coverage of the target neurons may be selected. For example, the electrode arrangement of FIG. 6C may be useful if the physician anticipates that the neural target will be closer to a distal tip of the lead body 510, while the electrode arrangement of FIG. 6D may be useful if the physician anticipates that the neural target will be closer to a proximal end of the lead body 510.

Any combination of ring electrodes 520 and segmented electrodes 530 may be disposed on the lead 500. For example, the lead may include a first ring electrode 520, two sets of segmented electrodes; each set formed of four segmented electrodes 530, and a final ring electrode 520 at the end of the lead. This configuration may simply be referred to as a 1-4-4-1 configuration (FIGS. 6A and 6E). It may be useful to refer to the electrodes with this shorthand notation. Thus, the embodiment of FIG. 6C may be referred to as a 1-1-4-4 configuration, while the embodiment of FIG. 6D may be referred to as a 4-4-1-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 530 are disposed on the lead. Another electrode configuration is a 1-3-3-1 configuration with two sets of segmented electrodes, each set containing three electrodes disposed around the circumference of the lead, flanked by two ring electrodes or a ring electrode and a tip electrode. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

When the lead 500 includes a plurality of sets of segmented electrodes 530, it may be desirable to form the lead 500 such that corresponding electrodes of different sets of segmented electrodes 530 are longitudinally aligned with one another along the length of the lead 500 (see e.g., the segmented electrodes 530 shown in FIG. 5). Longitudinal alignment between corresponding electrodes of different sets of segmented electrodes 530 along the length of the lead 500 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 500 are longitudinally aligned with one another and do not circumferentially shift in relation to one another during manufacturing of the lead 500.

In other embodiments, individual electrodes in the two sets of segmented electrodes 530 are staggered (see, FIG. 6B) relative to one another along the length of the lead body 510. In some cases, the staggered positioning of corresponding electrodes of different sets of segmented electrodes along the length of the lead 500 may be designed for a specific application.

FIGS. 6A-6E illustrate leads 600 with segmented electrodes 630, optional ring electrodes 620 or tip electrodes 620a, and a lead body 610. The sets of segmented electrodes 630 include either two (FIG. 6B) or four (FIGS. 6A, 6C, and 6D) or any other number of segmented electrodes including, for example, three, five, six, or more.

Any other suitable arrangements of segmented electrodes can be used. As an example, arrangements in which segmented electrodes are arranged helically with respect to each other. One embodiment includes a double helix.

As mentioned above (FIG. 6E), a tip electrode can be used in combination with one or more circumferential electrodes (e.g., one or more ring electrodes, one or more segmented electrodes, or any combination of one or more ring electrodes and one or more segmented electrodes). In at least some embodiments, a tip electrode may be selected to have the same, or substantially the same, surface area as one or more ring electrodes of the lead.

Turning to FIGS. 7A-14B, at least some connectors include retention assemblies for retaining a portion of a lead or lead extension in the connector. Retention assemblies may enlarge the circumference of the connector. For example, at least some known retention assemblies may include a threaded aperture that extends along a plane that is transverse to a longitudinal length of the connector and that receives a fastener that presses against a received lead or lead extension. Enlarging the circumference of the connector may be undesirable because it may be uncomfortable to the patient and may limit the locations where the connector can be implanted. Additionally, at least some known retention assemblies are formed from stainless steel and are covered by a septum to prevent fluid ingress into the connector. In which case, current leakage may occur if the septum is damaged.

As herein described, an improved connector (see e.g., 420 of FIG. 4) includes a retention assembly that includes a deformable gasket that retains a device (such as a lead or lead extension) within the connector by longitudinally compressing the gasket. The longitudinal compression of the gasket causes a corresponding radial expansion of the gasket towards the device within the connector. In at least some embodiments, the radial expansion of the gasket retains the device within the connector. In at least some embodiments, the radial expansion forms a watertight seal between the connector and the retained device. In a least some embodiments, the connector has a smaller circumference than a conventional connector having a retention assembly that includes a transverse threaded aperture.

The connector can be disposed along any suitable implantable medical device including, for example, a lead extension, a control module, a lead anchor, or the like. In some embodiments, the disclosed connector can be used for coupling an electrical stimulation lead to a lead extension. For example, the connector 420, shown in FIG. 4, is suitable for connecting the elongate device 300 to the lead extension body 406.

FIGS. 7A-7D illustrate one embodiment of the connector 420 disposed along a distal end portion of the lead extension 402. FIG. 7A illustrates, in side view, one embodiment of the contact housing 430 of the connector 420. The contact housing 430 is an elongate member having a first end portion 706, an opposing second end portion 708, and an exterior surface 732. The contact housing 430 defines a contact-housing lumen 792a suitable for receiving a portion of an elongated device, such as a lead or a lead extension, within the contact housing 430.

In some embodiments, the contact housing 430 is a tubular structure having an outer diameter larger than the outer diameter of the lead extension body 406. In some other embodiments, the contact housing 430 is isodiametric with the lead extension body 406. The contact housing 430 and the lead extension body 406 may be a unitary structure or can be formed as two separate structures that are permanently, or detachably, coupled together.

The contact housing 430 has a length and an inner diameter suitable for receiving a portion of an elongated device, such as the elongated device 300, in the contact-housing lumen 792a. Connector contacts 424 are exposed to contact-housing lumen 792a. In at least some embodiments, the connector contacts 424 are suitable for electrically coupling to terminals disposed along an elongated device when the elongated device is received by the contact-housing lumen 792a.

A retention member 710 is disposed along the second end portion 708 of the contact housing 430. The retention member 710 defines a retention-member lumen 792b extending along the entire length of the retention member 710. The retention-member lumen 792b opens to, and is aligned with, the contact-housing lumen 792a. The contact housing 430 can form a unitary structure with the retention member 710, or can be formed as two separate structures that are permanently, or detachably, coupled to one another.

In some embodiments, the retention member 710 is a tubular structure extending outwardly from the second end portion 708 in a direction that is parallel to the longitudinal length of the contact housing 430. In at least some embodiments, the retention member 710 has an outer diameter that is smaller than an outer diameter of the contact housing 430. In some embodiments, a thread 712 is disposed along an exterior surface of the retention member 710.

FIG. 7B illustrates, in longitudinal cross-sectional view, one embodiment of the gasket housing 440 suitable for coupling with the contact housing 430. In at least some embodiments, the gasket housing 440 is an elongate member having a first end portion 736 and an opposing second end portion 738. The gasket housing 440 has an exterior surface 742 and a gasket-housing lumen 792c extending between the first end portion 736 and the second end portion 738. The contact housing 430 and the gasket housing 440 can be either permanently coupled to one another or completely separable from one another. In at least some embodiments, the gasket housing 440 and the contact housing 430 are isodiametric with one another.

The gasket housing 440 includes a retention socket 744 defined along the first end portion 736 of the gasket housing 440. The retention socket 744 is suitable for receiving the retention member 710. The retention socket 744 includes a rear wall 746 and a side wall 748. In at least some embodiments, the rear wall 746 is disposed along the second end portion 738 of the gasket housing 440. In some embodiments, the side wall 748 includes a threaded portion 750 having a thread suitable to mate with the thread 712 of the retention member 710. In at least some embodiments, the gasket-housing lumen 792c extends through the rear wall 746 of the retention socket 744.

A gasket 760 is disposed in the gasket housing 440. In at least some embodiments, the gasket 760 is disposed in the retention socket 744. In some embodiments, the gasket 760 is disposed in a pocket 752 defined in the retention socket 744 along the rear wall 746. The gasket 760 can be of any suitable shape to dispose within the gasket housing 440. The gasket 760 defines a gasket lumen 792d extending through the length of the gasket 760. In FIG. 7B, the gasket 760 is shown as being torus-shaped. The gasket 760 is deformable and can change shape under compression and can regain its original shape when such compression is released.

The gasket 760 has a length suitable for expanding radially when compressed longitudinally. In addition, the material of the gasket 760 may be chosen such that longitudinal compression of the gasket 760 causes radial expansion of the gasket 760. Some example of such materials includes flexible polymers, rubber, silicone, or the like or their combinations thereof. In some embodiments, the material of the gasket 760 is chosen to form a watertight seal when tightened against an outer surface of a received elongated device.

FIG. 7C illustrates, in longitudinal cross-sectional view, one embodiment of the contact housing 430 partially coupled to the gasket housing 440 to form the connector 420. FIG. 7D illustrates, in end view, one embodiment of the connector 420. The contact housing 430 and the gasket housing 440 are partially coupled to one another by inserting the retention member 710 into the retention socket 744. The partial coupling of the gasket housing 440 and the contact housing 430 aligns the contact-housing lumen 792a, the retention-member lumen 792b, the gasket-housing lumen 792c, and the gasket lumen 792d along the longitudinal length of the connector 420 to collectively form a lead lumen 792. The lead lumen 792 is suitable for receiving an elongated device, such as an electrical stimulation lead, a lead extension, a splitter, an adaptor, or the like.

The contact housing 430 can tighten against the gasket housing 440 by advancing the gasket housing 440 along the retention member 710 in a direction shown by directional arrow 754. In FIG. 7C (and in other figures), the contact housing 430 advances against the gasket housing 440 via the threads 712 of the retention member 710 and the threaded portion 750 of the side wall 748 of the retention socket 744. In at least some embodiments, the retention member 710 can be advanced within the retention socket 744 by rotating the gasket housing 440 relative to the retention member 710, like a nut over a screw. It will be understood that other mating techniques are contemplated including, for example, the mechanism described with reference to FIGS. 13A-14B.

When the retention member 710 advances far enough into the retention socket 744, the retention member 710 contacts, and then compresses, a portion of the gasket 760 along the longitudinal length of the connector 420 between a distal tip of the retention member 710 and the rear wall 746 of the retention socket 744. In at least some embodiments, the contact housing 430, the retention member 710, and the gasket housing 440 are made of materials that are harder than the gasket 760 such that the gasket 760 compresses when the retention member 710 and the gasket housing 440 are tightened against each other.

Turning to FIGS. 8A-8E, the compression of the gasket 760 along the longitudinal length of the connector 420 causes a corresponding radial expansion of the gasket 760 into the lumen 792. In at least some embodiments, the radial expansion of the gasket 760 constricts the portion of the lead lumen 792 extending along the gasket (the gasket lumen 792d). When an elongated device is received by the lead lumen 792, the radial expansion of the lead lumen 792 may retain the received elongated device. In at least some embodiments, radial expansion of the gasket 760 causes a watertight seal to be formed with the received elongated device.

Figure 8A:
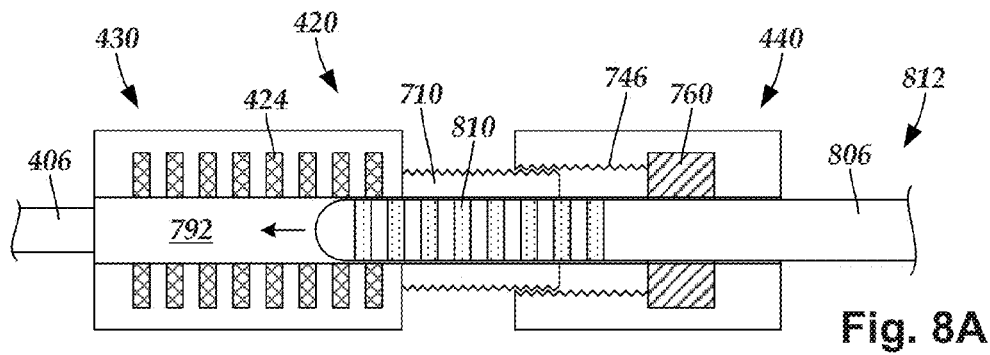
FIG. 8A is a schematic longitudinal cross-sectional view of one embodiment of a lead body partially inserted into the lead lumen of the connector of FIG. 7C, according to the invention.

FIG. 8A illustrates, in longitudinal cross-sectional view, one embodiment of a proximal end portion 812 of a body 806 of a lead partially inserted into the lead lumen 792 of the connector 420. The lead includes a plurality of terminals 810 disposed along the proximal end portion 812 of the lead. The gasket housing 440 is partially coupled to the contact housing 430 such that the retention member 710 is not in contact with the gasket 760.

Figure 8B:
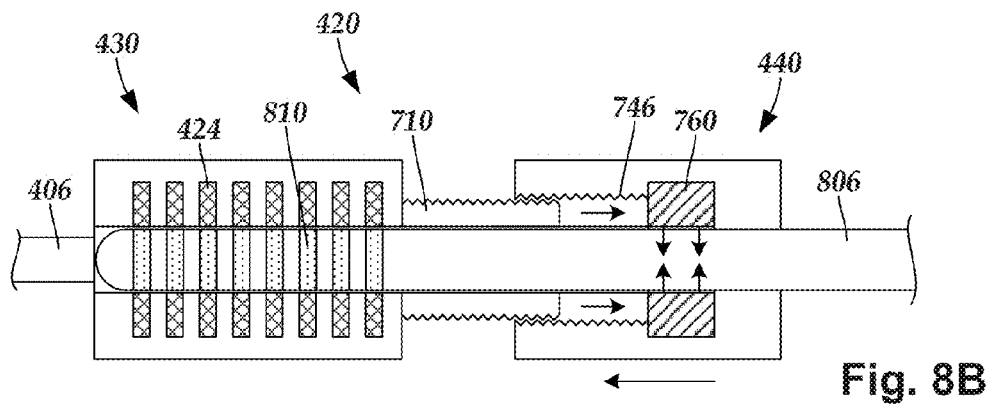
FIG. 8B is a schematic longitudinal cross-sectional view of one embodiment of the lead body of FIG. 8A fully inserted into the lead lumen of the connector of FIG. 7C, according to the invention.

FIG. 8B depicts the lead fully inserted into the lead lumen 792 of the connector 420 with the terminals 810 of the lead aligned with the connector contacts 424 in the contact housing 430, thereby coupling the terminals 810 to the connector contacts 424. In at least some embodiments, the coupling of the connector contacts 424 to the terminals 810 enables transmission of electrical signals from an electronic subassembly coupled to the connector contacts 424 to electrodes coupled to the terminals 810.

Figure 8C:
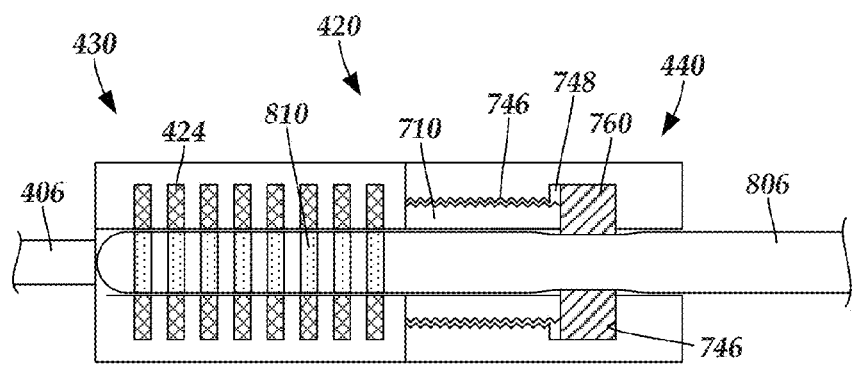
FIG. 8C is a schematic longitudinal cross-sectional view of one embodiment of the lead body of FIG. 8A fully inserted into the lead lumen of the connector of FIG. 7C and with the contact housing tightened toward the gasket housing such that the retention member compresses the gasket along a length of the connector, the compression of the gasket causing the gasket to expand radially into the lead lumen, thereby compressing toward a portion of the lead body disposed within the lumen, according to the invention.

FIG. 8C depicts the gasket housing 440 tightened against the contact housing 430. The retention member 710 compresses the gasket 760 in the retention socket 744 along the longitudinal length of the connector 420. The longitudinal compression of the gasket 760 causes the gasket 760 to expand radially into the lead lumen 792. In FIG. 8C, the radial expansion of the gasket 760 causes the gasket 760 to press against a portion of the lead disposed within the lead lumen 792. The radially-expanded gasket 760 grips and retains the lead within the connector 420. In some embodiments, a watertight seal is formed between the lead and the connector 420.

Figure 8D:
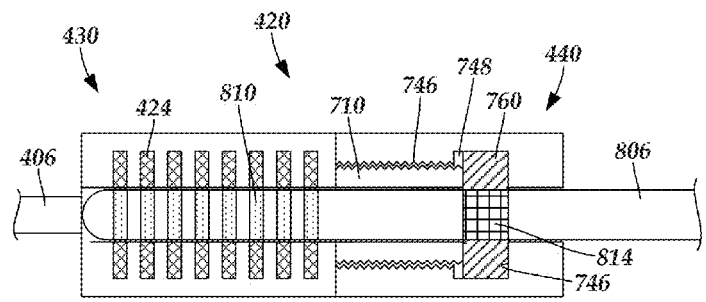
FIG. 8D is a schematic longitudinal cross-sectional view of one embodiment of the lead body of FIG. 8A fully inserted into the lead lumen of the connector of FIG. 7C and with the contact housing tightened toward the gasket housing such that the retention member squeezes the gasket along a length of the connector, the compression of the gasket causing the gasket to expand radially into the lead lumen, thereby compressing against a retention sleeve disposed along the lead body, according to the invention.

In at least some embodiments, as shown in FIG. 8D, a retention sleeve 814 is disposed along the proximal end portion of the lead 806. The retention sleeve 814 is a structure (for example, a band) that is either disposed over or within a portion of the lead. The retention sleeve 814 can be made of any suitable rigid material with such as stainless steel, polyvinyl chloride (PVC) or the like. The retention sleeve 814 provides a lead surface along which the gasket 760 can be compressed without compressing the lead body 806. In some embodiments, the retention sleeve 814 has a rough outer surface to increase friction at the location where the retention sleeve 814 mates with the gasket 760. The increased friction between the retention sleeve 814 and the gasket 760 can further improve the retention of the lead in the connector 420.

Figure 8E:
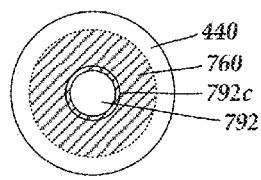
FIG. 8E is a schematic end view of one embodiment of the connector housing and gasket housing of FIG. 8C or 8D without the lead body of FIG. 8A inserted into the lead lumen of the connector housing and the gasket housing, the gasket expanding radially into the lumen as the retention member is longitudinally compressed, according to the invention.

FIG. 8E illustrates, in transverse cross-sectional view, one embodiment of the contact housing 430 tightened against the gasket housing 440 without the lead inserted into the lead lumen 792. As shown in FIG. 8E, the gasket 760 is expanded radially into the lead lumen 792 and narrows the lead lumen 792 along the portion 792c of the lead lumen extending through the gasket 760.

Figure 9:
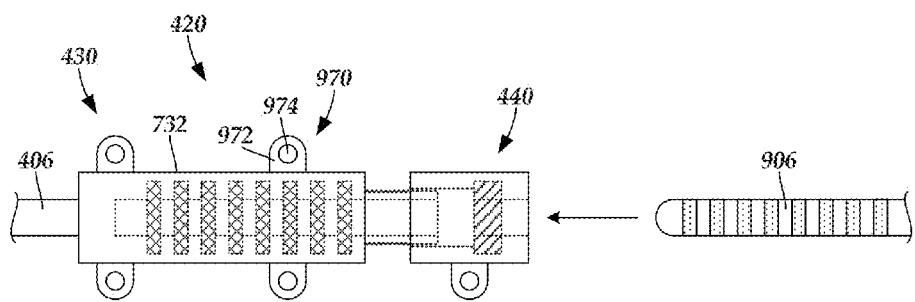
FIG. 9 is a schematic side view of one embodiment of the connector of FIG. 7C and a lead body suitable for insertion into a lead lumen of the connector, the connector including anchoring units disposed along exterior surfaces of the connector, according to the invention.

Turning to FIG. 9, in at least some embodiments the connector is suitable for anchoring to patient tissue. Anchoring the connector to patient tissue may reduce, or even prevent, undesired movement of the connector relative to the patient subsequent to an implantation procedure. Any suitable type of anchoring mechanisms may be used including, for example, suture sleeve, clips, or the like or combinations thereof.

FIG. 9 illustrates, in side view, one embodiment of the connector 420 and a proximal end portion of the body 906 of a lead suitable for insertion into a lead lumen 792 of the connector 420. The connector 420 includes anchoring units 970 disposed along the exterior surface 732 of the connector 420. The anchoring units 970 can be disposed along the contact housing 430, or the gasket housing 440, or both.

In some embodiments, the anchoring units 970 include anchoring tabs 972 extending outwardly from the exterior surface of the connector 420. Each anchoring tab 972 includes at least one anchoring aperture 974 that can be used to anchor (e.g., suture, staple, or the like or combinations thereof) the connector 420 to patient tissue. It will be understood that the connector 420 can include any suitable number of anchoring units 970 including, for example, one, two, three, four, five, six, seven, eight, or more anchoring units 970. The anchoring units 970 may be a formed as a part of the connector 420. Alternately, the anchoring units 970 may be formed along another component, such as a sleeve, that can be disposed over the connector 420.

Figure 10:
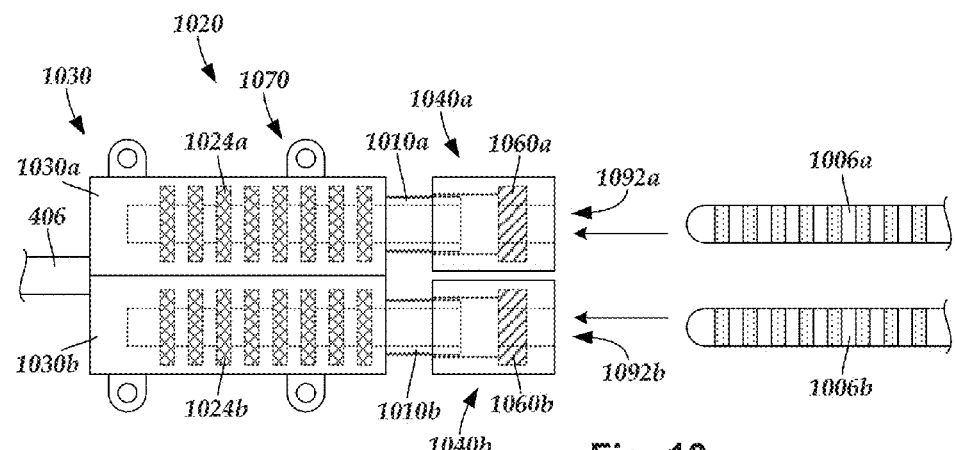
FIG. 10 is a schematic side view of one embodiment of a connector housing suitable for receiving multiple lead bodies, according to the invention.

Turning to FIG. 10, in some embodiments a connector may be suitable for receiving multiple electrical stimulation lead bodies. The multiple lead bodies can be from the same lead or from different leads. FIG. 10 illustrates, in side view, one embodiment of a connector 1020 suitable for receiving portions of two bodies 1006a and 1006b of one or more leads. In at least some embodiments, the connector 1020 includes a contact housing 1030 formed by attaching two contact housings 1030a and 1030b as a unitary structure or as two separate structures that are permanently, or detachably, coupled together. In FIG. 10, the contact housings 1030a and 1030b are shown in a side-by-side configuration. Other configurations are contemplated. In FIG. 10, two contact housings are shown. In at least some embodiments, the connector 1020 includes more than two contact housings.

The connector housings 1030a and 1030b define lead lumens 1092a and 1092b, respectively, and two pluralities of connector contacts: first connector contacts 1024a, and second connector contacts 1024b, open to the lead lumens 1092a and 1092b, respectively. In some embodiments, the connector contacts 1024a and 1024b each include eight connector contacts.

A gasket housing 1040a couples with connector housing 1030a via a retention member 1010a. A deformable gasket 1060a is disposed in the gasket housing 1040a. The lead lumen 1092a, which is suitable for receiving and retaining the lead body 1006a, extends through each of: the gasket housing 1040a, the retention member 1010a, and the contact housing 1030a.

Similarly, a gasket housing 1040b couples with connector housing 1030b via a retention member 1010b. A deformable gasket 1060b is disposed in the gasket housing 1040b. The lead lumen 1092b, which is suitable for receiving and retaining the lead body 1006b, extends through each of: the gasket housing 1040b, the retention member 1010b, and the contact housing 1030b.

Optionally, the connector 1020 includes one or more anchoring units 1070 suitable for anchoring the connector 1020 to patient tissue. The one or more anchoring units 1070 can be disposed along the contact housing 103, or the gasket housing 1040a, or the gasket housing 1040b, or some combination thereof.

Figure 11:
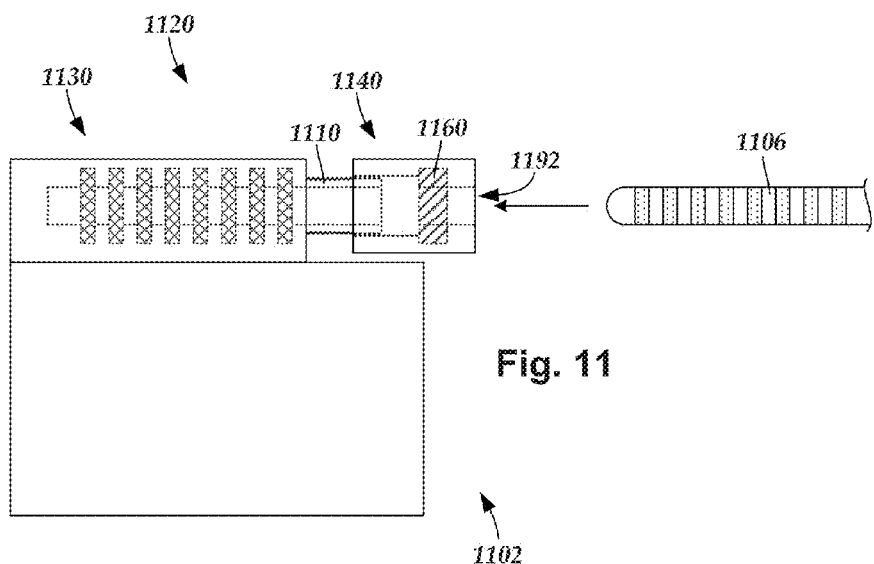
FIG. 11 is a schematic side view of one embodiment of a connector suitable for receiving a lead body, the connector disposed on a control module, according to the invention.

Turning to FIG. 11, in at least some embodiments the connector is disposed along a control module. FIG. 11 illustrates, in side view, one embodiment of a control module connector 1120 suitable for receiving a proximal end portion of a body 1106 of a lead. The connector 1120 is disposed along an outer surface of a control module 1102. In at least some embodiments, the non-connector portions of the control module 1102 are similar in structure and function as the control module 102 (shown in FIG. 1 and other figures). The connector 1120 is similar in structure and function to connector 420 (shown in FIG. 4 and other figures), and includes a lumen 1192 extending through a connector housing 1130 with connector contacts, a gasket housing 1140, a deformable gasket 1160, and a retention member 1110.

Turning to FIG. 12, in at least some embodiments the connector can be used with an implantable medical device that does not include connector contacts for making an electrical connection with a received elongated member, such as a lead anchor. FIG. 12 illustrates, in side view, one embodiment of a portion of a body 1206 of a lead retained by a lead anchor 1202. The lead anchor 1202 includes a retention member 1210 disposed along a retention member housing 1230, a gasket 1260 disposed in a gasket housing 1240, and a lead lumen that is suitable for receiving the lead body 1206 and that extends entirely through each of: the retention member 1210, the retention member housing 1230, the gasket 1260, and the gasket housing 1240. In at least some embodiments, the gasket housing 1240 is suitable for tightening against the retention member housing 1230 and longitudinally compressing the gasket 1260, as described above, with reference to FIGS. 7A-8E.

The lead anchor 1202 includes one or more anchoring units, such as anchoring unit 1270 (similar to the anchoring units 970 shown in FIG. 9), disposed along the external surface of the lead anchor 1202. The one or more anchoring units 1270 are suitable for anchoring the lead anchor 1202 to patient tissue.

In some embodiments, to anchor the lead body 1206 to patient tissue, the lead body 1206 is extended through the lead anchor 1202. The lead anchor 1202 is positioned at a desired location along the lead body 1206 and the gasket housing 1240 is tightened against the retention member housing 1230 to retain the lead body 1206 within the lead anchor 1202. The lead anchor 1202 can be sutured or stapled to patient tissue using the anchoring units 1270 either before or after the lead body is retained in the lead anchor 1202.

Turning to FIGS. 13A-14B, a number of different mechanisms can be used for mating a housing, such as the contact housing or the retention member housing, to the gasket housing. In FIG. 7C, the retention member 710 and the retention socket 744 are shown having threads that mate with each other. As shown in FIG. 7C, the gasket housing 440 is rotatable along the retention member 710, like a nut over a screw, to couple the contact housing 430 and the gasket housing 440.

Alternately, in some embodiments a retention mechanism includes one or more biasing members, a passageway, and a protrusion. The passageway and the protrusion may form a mechanism for advancing the gasket housing relative to the retention member. The biasing member may bias the retention member along the longitudinal length of the connector to releasably lock the gasket housing in a tightened position with the retention member.

FIG. 13A illustrates, in longitudinal cross-sectional view, one embodiment of a retention member 1310 suitable for inserting into a retention socket 1344 of a gasket housing 1340. The retention member can be attached to a housing (not shown), such as a connector housing, or a retention member housing, or the like. The gasket housing 1340 includes a gasket 1360 and a biasing member 1376 disposed in the retention socket 1344. The biasing member 1376 is disposed in the retention socket 1344 adjacent to the gasket 1360. In at least some embodiments, the biasing member 1376 is disposed concentrically outwards from the gasket 1360.

The retention member 1310 can be advanced towards the gasket 1360 in the retention socket 1344 to mate the retention member 1310 with the gasket housing 1340 and retain a portion of the lead body 1306 within the gasket housing 1340. FIG. 13B shows the gasket housing 1340 in a tightened position against the retention member 1310 such that a portion the lead body 1306 is retained by the gasket 1360 within the gasket housing 1330. The retention member 1310 is shown longitudinally compressing the gasket 1360. As the retention member 1310 is advanced towards the gasket 1360, the biasing member 1376 biases the retention member 1310 along the longitudinal axis of the gasket housing 1340 in a direction shown by directional arrow 1377. As shown in FIG. 13B, advancement of the retention member 1310 into the retention socket 1344 is performed against the biasing force of the biasing member 1376. The biasing member 1376 can include a spring, elastic band, flexible arms, or the like that pushes the retention member 1310 away from the gasket 1360.

FIGS. 14A-14B illustrates a locking mechanism that can be used to lock the retention member 1310 in the tightened position against the gasket housing 1340. FIG. 14A illustrates, in side view, one embodiment of the retention member 1310 and the gasket housing 1340 in a partially coupled configuration (i.e., the retention member is not physically touching the gasket), such as is depicted in FIG. 13A. FIG. 14B illustrates, in side view, one embodiment of the retention member 1310 and the gasket housing 1340 in a tightened position (i.e., the retention member is compressing the gasket), such as is depicted in FIG. 13B.

The gasket housing 1340 defines a passageway 1482 formed along a side wall of the retention socket 1344 of the gasket housing 1340. The passageway 1482 is suitable for receiving a protrusion 1480 disposed along an outer surface of the retention member 1310. To move the retention member 1310 into the retention socket 1344, a user can move the gasket housing 1340 toward the retention member 1310 while slightly rotating the gasket housing 1340 as the protrusion 1480 moves along the passageway 1482.

The biasing member 1376 biases the retention member 1310 along the longitudinal axis in a direction that maintains the position of the protrusion 1480 at a terminus 1484 of the passageway 1482 (as shown in FIG. 14B). When the protrusion 1480 is positioned at the terminus 1484 of the passageway 1482, the gasket housing 1340 is tightened against the retention member 1310 and an inserted lead body, such as the lead body 1306, is retained within the gasket housing 1340, as shown in FIG. 13B.

In at least some embodiments, moving the gasket housing 1340 inward (against the biasing force of the biasing member 1376) while rotating the gasket housing 1340 removes the protrusion 1480 from the terminus 1484 of the passageway 1482, enabling the protrusion 1480 to follow the passageway 1482 away from the terminus, thereby uncoupling the gasket housing 1340 from the retention member 1310 (as shown in FIG. 13A) and enabling the inserted lead body to be released from the gasket housing. It will be understood that, alternately, the protrusion can be disposed along the gasket housing and the passageway can be formed along the retention member.

Figure 15:
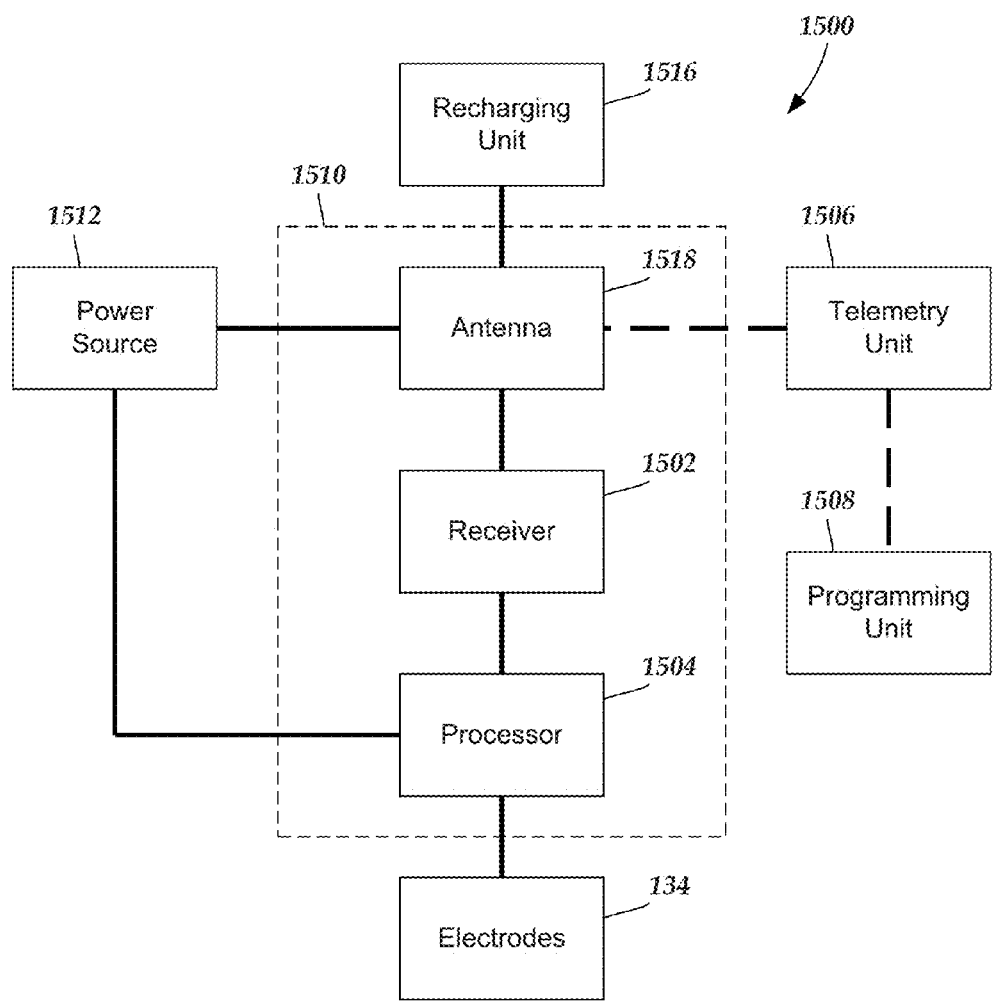
FIG. 15 is a schematic overview of one embodiment of components of a stimulation system, including an electronic subassembly disposed within a control module, according to the invention.

FIG. 15 is a schematic overview of one embodiment of components of an electrical stimulation system 1500 including an electronic subassembly 1510 disposed within a control module. It will be understood that the electrical stimulation system can include more, fewer, or different components and can have a variety of different configurations including those configurations disclosed in the stimulator references cited herein.

Some of the components (for example, a power source 1512, an antenna 1518, a receiver 1502, and a processor 1504) of the electrical stimulation system can be positioned on one or more circuit boards or similar carriers within a sealed housing of an implantable pulse generator, if desired. Any power source 1512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1518 or a secondary antenna. The external power source can be in a device that is mounted on the skin of the user or in a unit that is provided near the user on a permanent or periodic basis.

If the power source 1512 is a rechargeable battery, the battery may be recharged using the optional antenna 1518, if desired. Power can be provided to the battery for recharging by inductively coupling the battery through the antenna 1518 to a recharging unit 1516 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1504 is generally included to control the timing and electrical characteristics of the electrical stimulation system. For example, the processor 1504 can, if desired, control one or more of the timing, frequency, strength, duration, and waveform of the pulses. In addition, the processor 1504 can select which electrodes can be used to provide stimulation, if desired. In some embodiments, the processor 1504 selects which electrode(s) are cathodes and which electrode(s) are anodes. In some embodiments, the processor 1504 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 1504 is coupled to a receiver 1502 which, in turn, is coupled to the optional antenna 1518. This allows the processor 1504 to receive instructions from an external source to, for example, direct the pulse characteristics and the selection of electrodes, if desired.

In one embodiment, the antenna 1518 is capable of receiving signals (e.g., RF signals) from an external telemetry unit 1506 which is programmed by the programming unit 1508. The programming unit 1508 can be external to, or part of, the telemetry unit 1506. The telemetry unit 1506 can be a device that is worn on the skin of the user or can be carried by the user and can have a form similar to a pager, cellular phone, or remote control, if desired. As another alternative, the telemetry unit 1506 may not be worn or carried by the user but may only be available at a home station or at a clinician's office. The programming unit 1508 can be any unit that can provide information to the telemetry unit 1506 for transmission to the electrical stimulation system 1500. The programming unit 1508 can be part of the telemetry unit 1506 or can provide signals or information to the telemetry unit 1506 via a wireless or wired connection. One example of a suitable programming unit is a computer operated by the user or clinician to send signals to the telemetry unit 1506.

The signals sent to the processor 1504 via the antenna 1518 and the receiver 1502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1500 to cease operation, to start operation, to start charging the battery, or to stop charging the battery. In other embodiments, the stimulation system does not include the antenna 1518 or receiver 1502 and the processor 1504 operates as programmed.

Optionally, the electrical stimulation system 1500 may include a transmitter (not shown) coupled to the processor 1504 and the antenna 1518 for transmitting signals back to the telemetry unit 1506 or another unit capable of receiving the signals. For example, the electrical stimulation system 1500 may transmit signals indicating whether the electrical stimulation system 1500 is operating properly or not or indicating when the battery needs to be charged or the level of charge remaining in the battery. The processor 1504 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead extension for an electrical stimulation system, the lead extension comprising:
   a lead extension body having a distal end portion and a proximal end portion;
   a plurality of terminals disposed along the proximal end portion of the lead extension body;
   a connector disposed along the distal end portion of the lead extension body, the connector having an exterior surface and a longitudinal length, the connector comprising
      a contact housing having a first end portion, an opposing second end portion, and an exterior surface, the contact housing defining a contact-housing lumen and comprising a plurality of connector contacts disposed in the contact housing and exposed to the contact-housing lumen,
      a retention member disposed along the second end portion of the contact housing, the retention member defining a retention-member lumen extending along an entire length of the retention member,
      a gasket housing coupled to the second end portion of the contact housing, the gasket housing having a first end, an opposing second end, and an exterior surface,
      a retention socket defined along the first end of the gasket housing, the retention socket comprising a rear wall and a side wall, the retention socket configured and arranged for receiving the retention member, a gasket-housing lumen extending between the exterior surface of the gasket housing and the rear wall of the retention socket, a deformable gasket disposed in the retention socket and defining a gasket lumen, wherein the retention-member lumen, the contact-housing lumen, the gasket-housing lumen, and the gasket lumen collectively form a lead lumen configured and arranged for receiving a portion of an electrical stimulation lead, wherein the gasket housing is configured and arranged to tighten toward the contact housing by advancing the retention member into the retention socket and compressing the deformable gasket along the longitudinal length of the connector, the longitudinal compression of the gasket causing a corresponding radial expansion of the gasket into the lead lumen, the radial expansion of the gasket retaining a portion of the electrical stimulation lead within the lead lumen when the electrical stimulation lead is received by the lead lumen; and a plurality of conductors electrically coupling the plurality of terminals to the plurality of connector contacts.

2. The lead extension of claim 1, wherein the side wall of the retention socket comprises a threaded portion.

3. The lead extension of claim 2, wherein at least one thread is disposed along an exterior surface of the retention member, the at least one thread configured and arranged to mate with the threaded portion of the side wall of the retention socket.

4. The lead extension of claim 1, wherein the gasket is configured to form a watertight seal against the electrical stimulation lead when the gasket is radially expanded toward a portion of the electrical stimulation lead.

5. The lead extension of claim 1, wherein the connector further comprises at least one anchoring unit disposed along the exterior surface of the connector, the at least one anchoring unit configured and arranged for anchoring the connector to patient tissue when the connector is implanted in a patient.

6. The lead extension of claim 5, wherein the at least one anchoring unit comprises an anchoring aperture defined in an anchor tab extending outwardly from the connector.

7. The lead extension of claim 1, wherein the gasket is disposed in a pocket defined in the retention socket.

8. The lead extension of claim 1, wherein the connector further comprises a biasing member disposed in the retention socket.

9. The lead extension of claim 1, wherein the retention member comprises a protrusion extending from an exterior surface of the retention member.

10. The lead extension of claim 9, wherein the side wall of the retention socket defines a passageway configured and arranged for receiving the protrusion.

11. The lead extension of claim 1, wherein the lead lumen is a first lead lumen configured and arranged for receiving a portion of the electrical stimulation lead, and wherein the connector defines a second lead lumen configured and arranged for receiving a portion of a second electrical stimulation lead.

12. A lead assembly comprising:
the lead extension of claim 1; and
the electrical stimulation lead comprising a lead body having a proximal end portion and a distal end portion, a plurality of electrodes disposed along the distal end portion of the lead body, a plurality of terminals disposed along the proximal end portion of the lead body, and a plurality of conductors electrically coupling the plurality of electrodes to the plurality of terminals;

wherein the proximal end portion of the lead body is configured and arranged for insertion into the lead lumen of the connector of the lead extension;

wherein the plurality of terminals of the electrical stimulation lead are configured and arranged for coupling with the plurality of connector contacts of the connector when the proximal end portion of the lead body is inserted into the lead lumen.

13. The lead assembly of claim 12, wherein the electrical stimulation lead further comprises a retention sleeve disposed along the proximal end portion of the lead body, and wherein the gasket of the connector is configured and arranged for tightening toward the retention sleeve when the electrical stimulation lead is inserted into the lead lumen and the retention member of the connector is advanced into the retention socket of the connector.

14. An electrical stimulating system comprising:
the lead assembly of claim 12; and
a control module coupleable to the lead assembly, the control module comprising
a housing,
an electronic subassembly disposed in the housing; and
a control-module connector for receiving the lead extension of the lead assembly, the connector comprising
a connector housing defining a port configured and arranged for receiving the proximal end portion of the body of the lead extension, and
a plurality of connector contacts disposed in the connector housing, the plurality of connector contacts configured and arranged to couple to the plurality of terminals of the lead extension when the proximal end portion of the lead extension body is received by the connector housing of the control-module connector.

15. A method of implanting an electrical stimulation lead, the method comprising:
providing the lead assembly of claim 12;
advancing the distal end portion of the electrical stimulation lead of the lead assembly to a target stimulation location within a patient;
inserting the proximal end portion of the electrical stimulation lead into the lead lumen of the connector of the lead extension of the lead assembly; and
retaining the proximal end portion of the electrical stimulation lead in the lead lumen by advancing the retention member of the connector housing of the connector into the retention socket of the gasket housing of the connector, the advancement of the retention member into the retention socket causing the deformable gasket of the connector to compress along the longitudinal length of the connector, the longitudinal compression of the gasket causing a corresponding radial expansion of the gasket into the lead lumen, the radial expansion of the gasket retaining the proximal end portion of the electrical stimulation lead within the lead lumen.

16. The method of claim 15, wherein retaining the proximal end portion of the electrical stimulation lead in the lead lumen comprises forming a watertight seal between the gasket and the electrical stimulation lead.

* * * * *